United States Patent
Watanabe et al.

(10) Patent No.: US 9,864,022 B2
(45) Date of Patent: Jan. 9, 2018

(54) SUPERCONDUCTING MAGNET DEVICE AND MAGNETIC RESONANCE IMAGING DEVICE

(71) Applicant: HITACHI, LTD., Tokyo (JP)

(72) Inventors: Hiroyuki Watanabe, Tokyo (JP); Jun Kawamura, Hitachi (JP); Kunihiro Takayama, Tokyo (JP); Kazuyuki Suzuki, Tokyo (JP); Yousuke Nishikawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 440 days.

(21) Appl. No.: 14/422,539

(22) PCT Filed: Sep. 17, 2013

(86) PCT No.: PCT/JP2013/074962
§ 371 (c)(1),
(2) Date: Feb. 19, 2015

(87) PCT Pub. No.: WO2014/050621
PCT Pub. Date: Apr. 3, 2014

(65) Prior Publication Data
US 2015/0234018 A1    Aug. 20, 2015

(30) Foreign Application Priority Data

Sep. 27, 2012 (JP) .................. 2012-214199

(51) Int. Cl.
*G01R 33/34* (2006.01)
*G01R 33/385* (2006.01)
(Continued)

(52) U.S. Cl.
CPC .......... *G01R 33/34* (2013.01); *G01R 33/385* (2013.01); *G01R 33/42* (2013.01); *H01F 6/02* (2013.01)

(58) Field of Classification Search
CPC ............ G01R 33/3806; G01R 33/3815; G01R 33/421; G01R 33/3804; H01F 6/02; H01F 6/06
(Continued)

(56) References Cited

U.S. PATENT DOCUMENTS 5,982,260 A    11/1999 Byrne
7,498,814 B1 *  3/2009 Huang ............... G01R 33/3815
                                                      324/318
(Continued)

FOREIGN PATENT DOCUMENTS

JP    9-223620    8/1997
JP    2006-324411    11/2006
(Continued)

OTHER PUBLICATIONS

International Search Report in PCT/JP2013/074962.

*Primary Examiner* — Melissa Koval
*Assistant Examiner* — Rishi Patel
(74) *Attorney, Agent, or Firm* — Cooper & Dunham LLP

(57) ABSTRACT

The present invention is to provide a structure that can effectively reduce quench in an open superconducting magnet. In order to do so, a pair of superconducting magnets is respectively provided with a primary coil, a shield coil to suppress a leakage magnetic field of the primary coil, and a coil bobbin. The coil bobbin has a cylindrical part on which the primary coil is wound, a ring-shaped end plate on which the inner periphery part is fixed to an end of the imaging space side of the cylindrical part, and a support member preventing the outer periphery part of the ring-shaped end plate from being displaced on the imaging space side. Hence, deformation of the end plate is suppressed to prevent deformation of the primary coil. This can reduce quench caused by the deformation of the primary coil.

7 Claims, 8 Drawing Sheets

(51) Int. Cl.
*G01R 33/42* (2006.01)
*H01F 6/02* (2006.01)

(58) Field of Classification Search
USPC ........ 324/318, 319; 335/216, 299, 301, 302; 29/602.1
See application file for complete search history.

(56) References Cited

U.S. PATENT DOCUMENTS

| | | | |
|---|---|---|---|
| 2007/0152789 A1 | 7/2007 | Watanabe et al. | |
| 2010/0295640 A1* | 11/2010 | Tamura | G01R 33/3815 335/216 |
| 2011/0028327 A1* | 2/2011 | Kodama | H01F 6/065 505/211 |

FOREIGN PATENT DOCUMENTS

| | | |
|---|---|---|
| JP | 2007-208232 | 8/2007 |
| JP | 2010-200794 | 9/2010 |
| JP | 2010-233736 | 10/2010 |

\* cited by examiner

SUPERCONDUCTING MAGNET DEVICE AND MAGNETIC RESONANCE IMAGING DEVICE

TECHNICAL FIELD

The present invention relates to a superconducting magnet device using a superconducting magnet and a magnetic resonance imaging device (hereinafter, referred to as MRI (Magnetic Resonance Imaging) device) using the superconducting magnet device, and in particular to a superconducting magnet device hardly causing quench.

BACKGROUND ART

In an MRI apparatus, a superconducting magnet is used as a generation source of a strong static magnetic field. The superconducting magnet forms a superconducting coil for which a superconducting wire is wound on a coil bobbin and has a configuration fixed by filling the interspaces of the superconducting wire with resin. The superconducting magnet is cooled to a temperature (normally, for example, 4.2 Kelvin, the boiling point of liquid helium) at which the superconducting magnet transitions to a superconducting state; an electric current is applied to the superconducting coil to attain a rated magnetic field after cooling the superconducting magnet; and a circuit referred to as a superconducting switch is closed to reach a closed-loop state where a permanent current flows. Hence, the superconducting state can be maintained.

However, as described in Patent Literature 1, in a permanent current mode, if a superconducting wire of a superconducting coil is moved a few nm for some disturbance or if a crack is formed in resin fixing the superconducting wire, local heat is generated. If the temperature of the superconducting wire exceeds the critical temperature due to the heat generation, transition (quench) from superconduction to normal conduction is generated. If quench is generated, a large amount of liquid helium is consumed; liquid helium reinjection is required in order to activate the superconducting magnet again, which results in a loss of time and human resources.

Therefore, in Patent Literature 1, it is presumed that "secular change" of a superconducting coil is the cause of a superconducting wire being moved and a crack in resin, and the technique to accelerate a secular change of the inner structure of the superconducting coil substantially in advance by repeating magnetization and demagnetization of a superconducting magnet and applying an overcurrent is suggested. Hence, sudden quench hardly occurs during a period while a permanent current for a long time has been kept.

On the other hand, an open-type MRI device that does not provide a patient to be an object with a sense of limitation is known. In the open-type MRI device, an annular helium vessel in which liquid helium is filled is disposed symmetrically on the top and bottom across a space in which an object is to be disposed, and coil bobbins on which superconducting coils are wound are respectively accommodated in the vessel. In Patent Literature 2 and 3, an example of the coil bobbin structure in an open-type MRI device is disclosed.

CITATION LIST

Patent Literature

PTL 1: Japanese Unexamined Patent Application Publication No. 2006-324411

PTL 2: Japanese Unexamined Patent Application Publication No. Hei 9-223620

PTL 3: Japanese Unexamined Patent Application Publication No. 2007-208232

SUMMARY OF INVENTION

Technical Problem

A coil bobbin and a superconducting coil of a superconducting magnet is accommodated in a liquid helium vessel disposed in a vacuum chamber, and additionally, a permanent current is applied to the superconducting coil, which results in a state where a strong magnetic field is generated. Therefore, it is very difficult to grasp statuses of a superconducting coil, resin to fix the coil, as well as a coil bobbin. The technique in PTL 1 merely presumes that a superconducting wire is moved or that a crack is formed in resin due to a cause of quenching such as "secular change" of a superconducting coil.

The purpose of the present invention is to provide a structure where quench of an open-type superconducting magnet can be reduced effectively.

Solution to Problem

In the present embodiment, a support member is disposed to prevent a ring-shaped end plate fixed on an end of a cylindrical part where a main coil of a coil bobbin is wound from being deformed to a static magnetic field space side.

Advantageous Effects of Invention

Because a support member can prevent an end plate of a coil bobbin from deformation in the present invention, deformation of a main coil can be reduced efficiently. Hence, quench caused by deformation of the main coil can be suppressed.

DESCRIPTION OF EMBODIMENTS

The inventors checked how the inner structure of a superconducting magnet of an MRI device changed in a superconducting state in detail. Consequently, it was found that a specific structural change that could not occur in a cylindrical superconducting magnet device occurred in an open-type superconducting magnet device in which a pair of superconducting magnets was disposed opposite to each other across an imaging space. Specifically, it was found that a part of a coil bobbin holding a main coil of a superconducting coil was deformed by electromagnetic force acting on the main coil and generated distortion to the main coil in accordance with the coil bobbin deformation. If the main coil distortion becomes excessive, a crack is generated in impregnating resin filling a gap between superconducting wires or quench is generated by the superconducting wires being moved. It was found that the coil bobbin deformation was generated on a plate-shaped member (end plate) holding a main coil from the facing sides of a pair of the superconducting magnets.

Therefore, the present invention provides a structure that prevents a coil bobbin deformation and improves quench-proof property of a superconducting magnet. Specifically, in order to suppress coil deformation, a member that suppresses deformation of an end plate holding a main coil from the facing sides of superconducting magnets is disposed. Hereinafter, the description will be made in detail using diagrams.

First Embodiment

Figure 1:
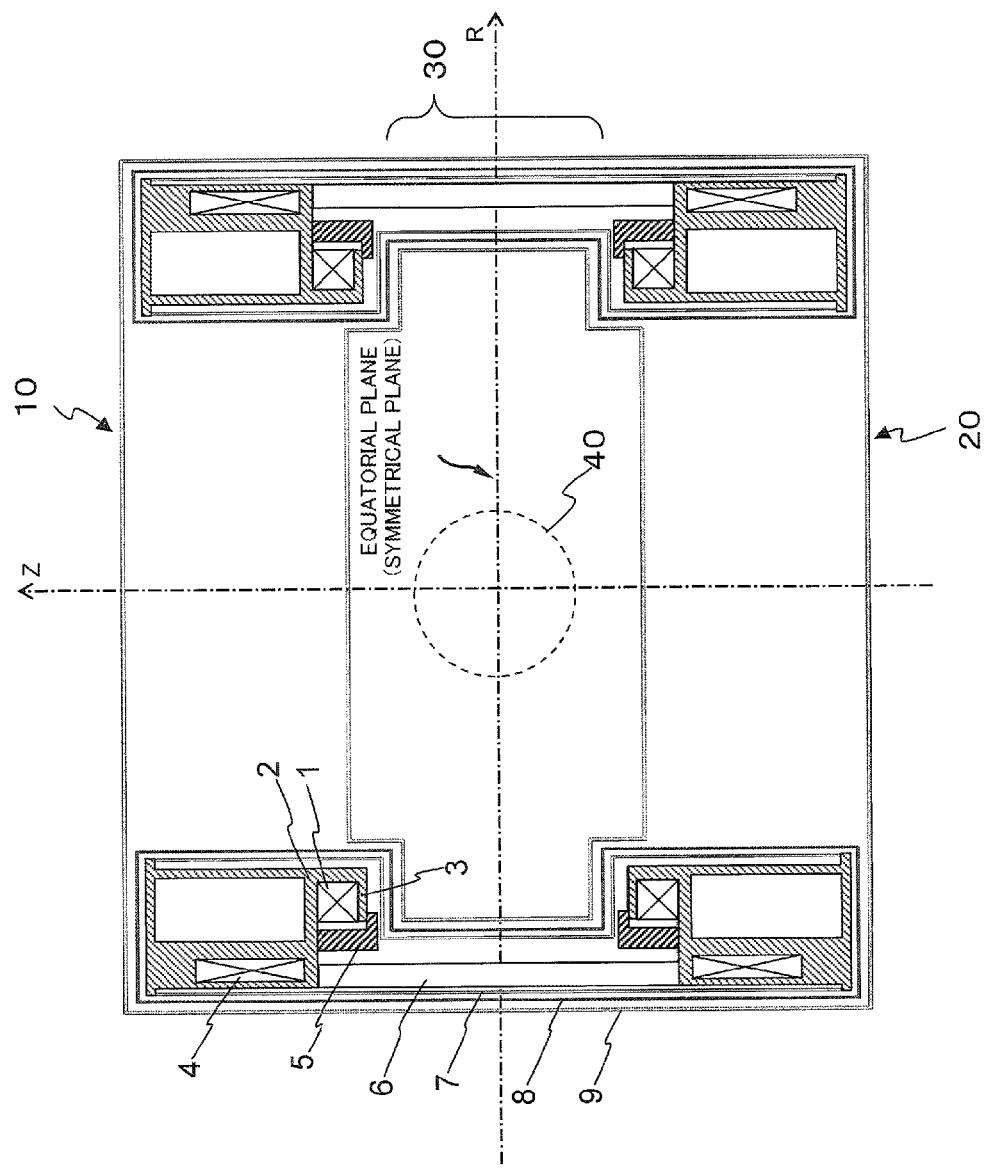
FIG. 1 is a cross-sectional diagram of a superconducting magnet device of the first embodiment.
Figure 2:
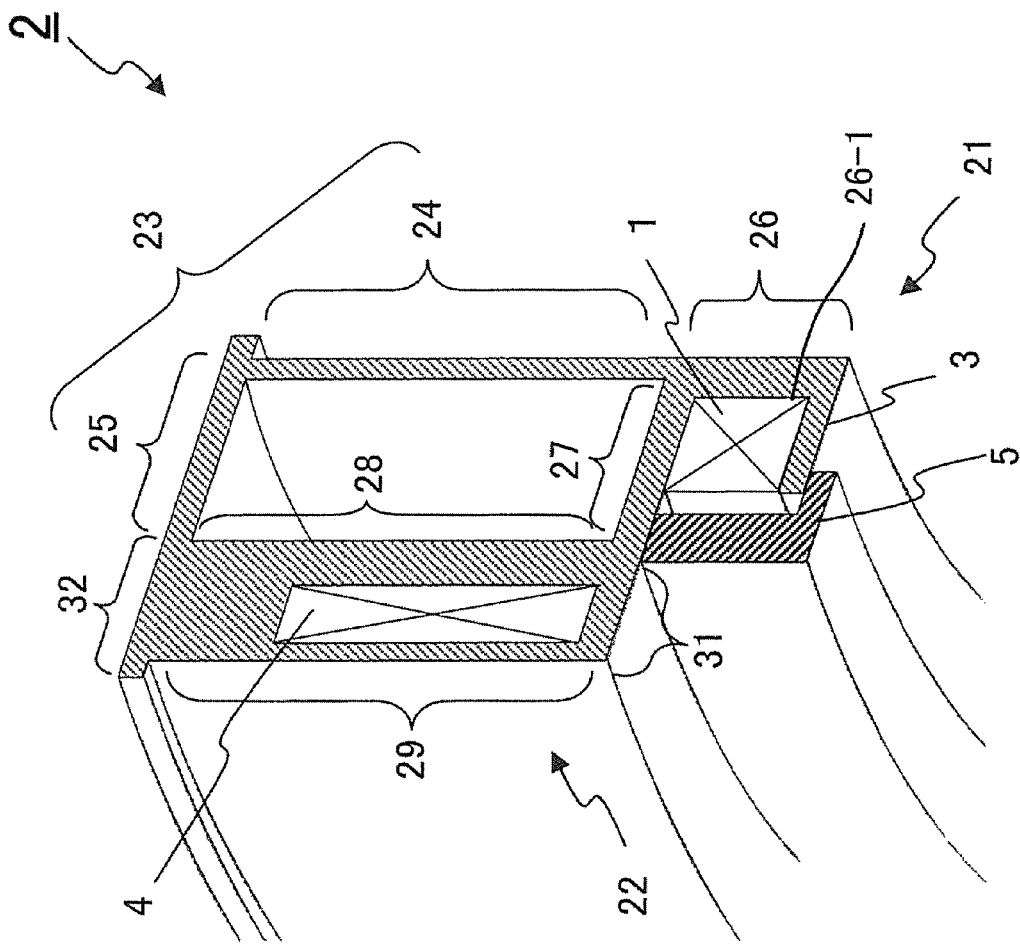
FIG. 2 is a cross-sectional perspective diagram of the coil bobbin 2 of the device in FIG. 1.

A superconducting magnet device of the first embodiment will be described using FIGS. 1 and 2. FIG. 1 is a cross-sectional diagram of an open-type superconducting magnet device of the first embodiment. FIG. 2 is a cross-sectional perspective diagram of a coil bobbin.

A superconducting magnet device has a pair of the superconducting magnets 10 and 20 disposed opposite to each other across the space (imaging space) 40 to create a static magnetic field and the connecting part 30 connecting a pair of the superconducting magnets 10 and 20. A pair of the superconducting magnets 10 and 20 is respectively comprised of the main coil 1, the shield coil 4 to suppress a leakage magnetic field of the main coil 1, and the coil bobbin 2. The coil bobbin 2 has the cylindrical part 26 on which the main coil 1 is wound, the ring-shaped end plate 3 whose inner periphery part is fixed to an end of the imaging space 40 side of the cylindrical part 26, and the support member 5 preventing the outer periphery part of the ring-shaped end plate 3 from being displaced on the imaging space 40 side.

For example, the coil bobbin 2 can include the ring-shaped opposite end plate 27 disposed on the opposite side to the imaging space 40 of the cylindrical part 26. The support member 5 can be a member with an L-shaped cross-section, and an end is fixed to the opposite end plate 27 in this case. The other end supports the outer periphery part of the ring-shaped end plate 3.

The above support member 5 can be a ring-shaped member along the ring-shaped end plate.

Hereinafter, the open-type superconducting magnet device of FIG. 1 will be further described specifically. The open-type superconducting magnet device of FIG. 1 is provided with a pair of the superconducting magnets 10 and 20 disposed facing each other in the vertical direction (Z direction) across the imaging space (a space to create a static magnetic field) 40 and the two connecting part 30 disposed between a pair of the superconducting magnets 10 and 20. The connecting part 30 supports the upper superconducting magnet 10 against the lower superconducting magnet 20 as well as connects the liquid helium vessels 7 in the respective insides.

The superconducting magnets 10 and 20 are respectively comprised of the annular coil bobbin 2, the main coil 1, the shield coil 4, the liquid helium vessel 7, the shield plate 8, and the vacuum vessel 9. Both of the main coil 1 and the shield coil 4 have a structure where an alloy-system superconducting wire such as NbTi (hereinafter, referred to as a superconducting wire) is wound in a predetermined position of the coil bobbin 2; and resin is impregnated in a gap of the superconducting wires to fix them. The coil bobbin 2 is comprised of non-magnetic metals (for example, SUS304 and aluminum alloy).

The main coils 1 of the superconducting magnets 10 and 20 respectively generate a magnetic field in the Z-axis direction in the imaging space 40. The shield coils 2 of the superconducting magnets 10 and 20 generate magnetic fields in the reverse Z-axis direction to the magnetic fields of the main coils 1 so as to cancel out leakage of the magnetic fields of the main coils 1 to the outside of the imaging space 40.

As shown in FIG. 2, the annular coil bobbin 2 has a structure where the main coil bobbin 21 for supporting the main coil 1, the shield coil bobbin 22 for supporting the shield coil 4, and the housing part 23 are connected. The housing part 23 connects and supports the main coil bobbin 21 and the shield coil bobbin 22. The main coil bobbin 21 is disposed on the closest side (facing surface) to the imaging space 40 by the housing part 23. The shield coil bobbin 22 is disposed in a position more remote than the main coil bobbin 21 from the imaging space 40 for the Z-axis direction and R-axis direction (radial direction).

The main coil bobbin 21 is comprised of the cylindrical part 26, the ring-shaped end plate 3, and the ring-shaped opposite end plate 27.

The end plate 3 is disposed at the end on the imaging space 40 side of the cylindrical part 26, the inner periphery part is fixed to the cylindrical part 26, and the outer periphery part is opened. That is, the end plate 3 has a structure where it is cantilever-supported by the cylindrical part 26.

The opposite end plate 27 is disposed at the opposite end to the imaging space 40 of the cylindrical part 26. The inner periphery part of the opposite end plate 27 is fixed to the cylindrical part 26, and the outer periphery part is fixed to the shield coil bobbin 22. Hence, the opposite end plate 27 connects the main coil bobbin 21 and the shield coil bobbin 22.

A superconducting wire of the main coil 1 is wound around a space in which three sides are surrounded by the inner periphery plate 26-1 of the cylindrical part 26, the end plate 3, and the opposite end plate 27 from the open outer periphery side of the main coil bobbin 21. Resin is impregnated in a gap between superconducting wires to fix them.

A main electromagnetic force acting on the main coil 1 wound on the main coil bobbin 21 is comprised of a repulsive force against the shield coil 4 supported by the same coil bobbin 2 and an attractive force to the main coils 1 of the coil bobbins 2 disposed facing each other across the imaging space 40, and the main electromagnetic force is that acting on the equatorial plane side in the Z direction.

Also, in order to secure the height of the imaging space 40 as high as possible and improve a static magnetic field strength with the main coil 1 approaching the imaging space 40, the end plate 3 of the main coil bobbin 21 is designed to secure a required rigidity and to be as thin as possible.

The shield coil bobbin 22 is comprised of the ring-shaped inner cylinder 28 and outer cylinder 29, the ring-shaped end plate 31, and the ring-shaped opposite end plate 32. The inner periphery part and outer periphery part of the ring-shaped end plate 31 are fixed at the lower ends of the inner cylinder 28 and outer cylinder 29 respectively. The inner periphery part and outer periphery part of the ring-shaped opposite end plate 32 are fixed at the lower ends of the inner cylinder 28 and outer cylinder 29 respectively. The shield coil 4 is wound around a space in which four sides are surrounded by the ring-shaped inner cylinder 28, the outer cylinder 29, the ring-shaped end plate 31, and the ring-shaped opposite end plate 32. Resin is impregnated in a gap between superconducting wires to fix them.

The housing 23 is provided with the inner cylinder 24 and the ring-shaped end plate 25 fixed at the end opposite to the imaging space 40 of the inner cylinder 24. At the end on the imaging space 40 side of the inner cylinder 24, the cylindrical part 26 of the main coil bobbin 21 is fixed. The outer periphery part of the end plate 25 is fixed to the shield coil bobbin 22.

The respective parts of the coil bobbins 2 are fixed securely by welding and screwing.

Also, the ring-shaped support member 5 supporting the outer periphery side end that is not supported of the end plate 3 of the main coil bobbin 21 in the vertical direction (Z-axis direction) is disposed for the coil bobbin 2 of the present invention. The support member 5 has an L-shaped cross-section as shown in FIG. 2, and the upper end is securely fixed to the end plate 31 of the opposite end plate 27 of the main coil bobbin 21 or the shield coil bobbin 22 by welding etc.

The top of the lower end of the support member 5 is located on the imaging space 40 side closer than the top of the end plate 3 for the Z-axis direction and prevents the top of the end plate 3 from being displaced on the imaging space 40 side for the Z-axis direction. The support member 5 is comprised of non-magnetic metals (for example, SUS304 and aluminum alloy) similarly to the coil bobbin 2.

The coil bobbin 2 of the lower superconducting magnet 20 has a structure where it is symmetrical with respect to the coil bobbin 2 of the upper superconducting magnet 10 across the equatorial plane (facing surface).

Next, the outer structure of the coil bobbin 2 will be described. The liquid helium vessel 7, as shown in FIG. 1, is fixed at the inner-periphery-side end of the end plate 25 as well as the outer-periphery-side end of the end plate 32 and creates a space to be filled with liquid helium around the coil bobbin 2. The outsides of the liquid helium vessel 7, the end plate 25, and the end plate 32 are covered with the shield plate 8. On the outside of the shield plate 8, the vacuum vessel 9 is installed.

The connecting part 30 connecting the upper and lower superconducting magnets 10 and 20 is provided with the connecting column 6 connecting the coil bobbin 2 of the upper superconducting magnet 10 and the coil bobbin 2 of the lower superconducting magnet 20. The connecting column 6 supports the main coil 1 as well as the shield coil 4 of the upper superconducting magnet 10 and the main coil 1 as well as the shield coil 4 of the lower superconducting magnet 20 with a force against electromagnetic attraction acting between them. The surrounding of the connecting column 6 is covered with the liquid helium vessel 7, the shield plate 8, and the vacuum vessel 9. These are respectively connected to the upper and lower superconducting magnets.

In a superconducting magnet device with such a structure, in case of the coil bobbin 2 for which the support member 5 is not disposed, the open outer periphery part of the end plate 3 of the main coil bobbin 21 is displaced on the equatorial plane (imaging space 40) side. Specifically, the outer periphery part of the end plate 3 is displaced by being pulled out in the Z-axis direction, and the end plate 3 is changed to the disc spring shape and is bent and deformed in the radial direction.

The bending direction is concave to the equatorial plane (imaging space 40).

According to the deformation, the end of the outer periphery part of the main coil 1 is displaced in the Z-axis direction following the shape of the end plate 3 and is bent and deformed in the radial direction. Due to the deformation, displacement and distortion occur to a coil, which results in cracking of impregnated resin that comprises the coil or causing coil quench by moving a conductor and generating friction heat.

Figure 3:
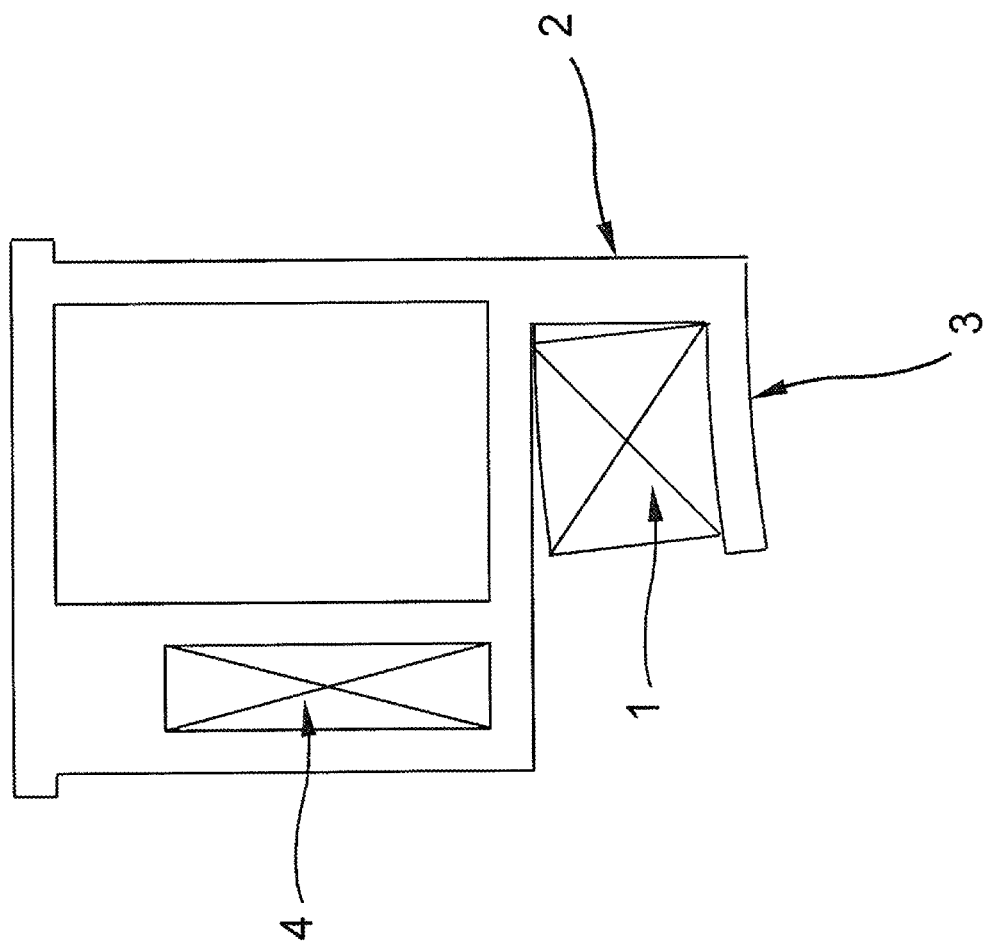
FIG. 3 is an explanatory diagram showing deformation of an end plate and the main coil 1 in a case where the coil bobbin 2 is not provided with a support member.
Figure 4:
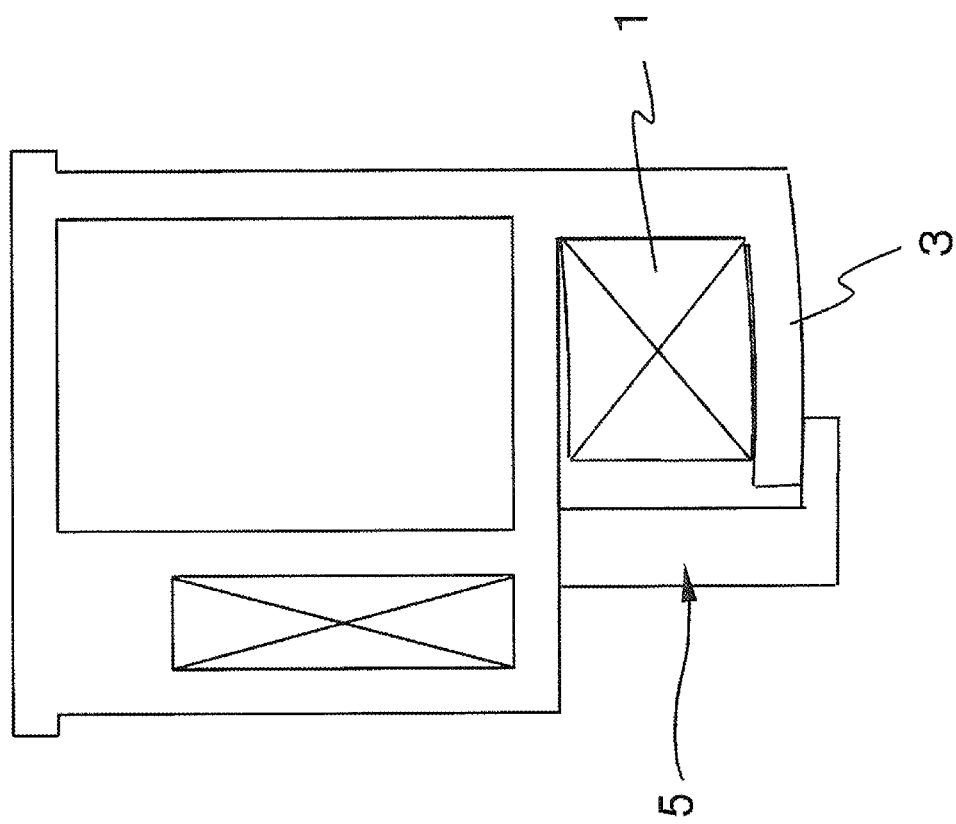
FIG. 4 is an explanatory diagram showing deformation of the main coil 1 and an end plate of the coil bobbin 2 provided with a support member of FIG. 1.

However, in the present invention, as shown in FIG. 2, the support member 5 supports the end of the open side (outer periphery side) of the end plate 3 in the Z direction and prevents the tip of the end plate 3 from being displaced in the Z-axis direction as shown in FIG. 4 even if an electromagnetic forth attracting each other is generated in the main coils 1 of the upper and lower superconducting magnets 10 and 20 in a superconducting state. Hence, the center part of the radial direction width of the end plate 3 is bent convexly toward the imaging space 40, but the displacement of the tip is prevented by the support member 5, and the displacement size of the entire end plate 3 is smaller than the case of FIG. 3. Although the main coil 1 deforms following the bend of the end plate 3, displacement by simple bend becomes the main part, and distortion is suppressed. Although the distortion (stress) generated to the main coil 1 is changed depending on a bobbin shape and an end plate thickness, as an example, the stress by an electromagnetic force to be applied to the main coil 1 can be reduced to 30 to 40% in a case with the support member 5 compared to a case without the support member 5 if the bobbin shape and the end plate thickness are the same.

Thus, in the present embodiment, a stress to be applied to the main coil 1 can be reduced by disposing the support member 5 and restricting deformation of the end plate 3 of the main coil bobbin 21 due to an electromagnetic force to be applied to the main coil 1, which can prevent quench caused by the deformation of the main coil 1.

Additionally, the part where the support member 5 supports the end plate 3 may be fixed by welding or screwing even in a state where the member and plate only come into contact with each other.

Also, it can be designed so that a gap with a predetermined height is created in a state where an electric current is not applied to the main coil 1 between the support member 5 and the end plate 3. In this case, when a magnetic field is generated by applying an electric current to the main coil 1, deformation can be allowed until the end plate 3 comes into contact with the support member 5.

Additionally, although a case where the main coil 1 and the shield coil 4 are made of materials that become a superconducting state at a liquid helium temperature was described in the first embodiment, there is a case where the liquid helium vessel 7 and the shield plate 8 are unnecessary if these are comprised of a high-temperature superconductor.

Also, the main coil 1 and the shield coil 4 can be comprised of a plurality of coils.

Second Embodiment

An open-type superconducting magnet device of the second embodiment will be described using FIG. 5.

In the second embodiment, the support member 5 is a plurality of members disposed along the peripheral direction of the ring-shaped end plate 3. In this case, a plurality of members of the support member 5 can be disposed at intervals mutually.

Figure 5:
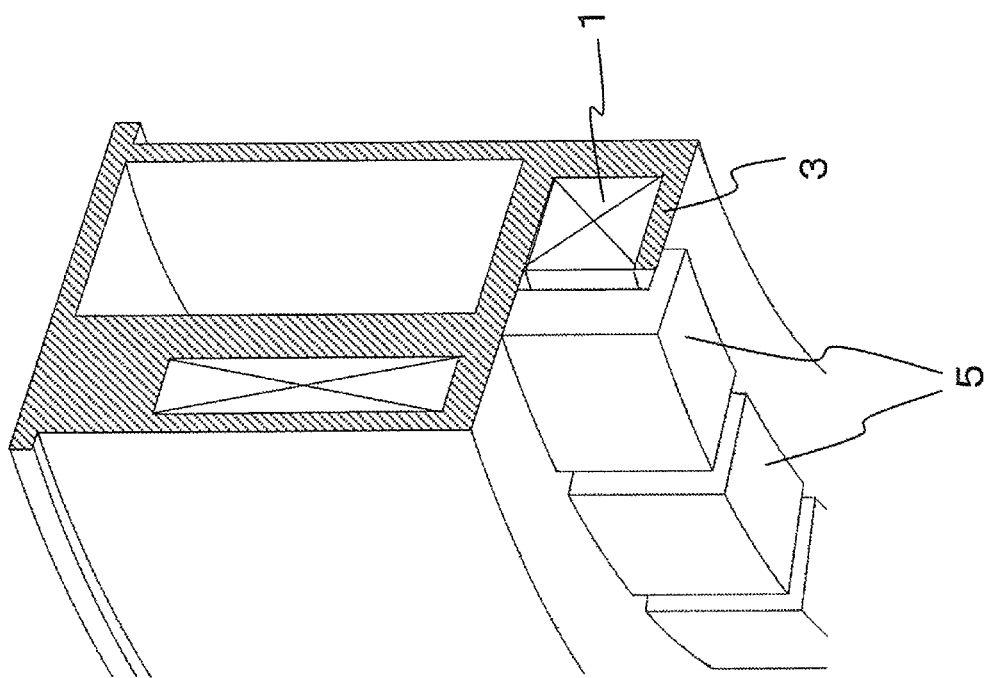
FIG. 5 is a cross-sectional perspective diagram of the coil bobbin 2 provided with the support member 5 of the second embodiment.

Specifically, in the configuration of FIG. 5, the ring-shaped support member 5 is divided into a plurality of members in the peripheral direction. A plurality of the divided support members 5 are disposed at predetermined intervals in the peripheral direction. Such a divided structure can easily pull out the electric current supply end of a superconducting wire of the main coil 1 from the coil bobbin 2. Also, attaching the support member 5 to the coil bobbin 2 becomes easier.

Also, although FIG. 5 shows the support members 5 into which the ring-shaped support member 5 is divided, the inner and outer peripheral shapes of the support members 5 is not necessarily needed to be arc but may also be linear. By using the linear support members, the manufacturing cost can be reduced than the arc support members.

In the second embodiment, the structure other than the support member 5 is similar to the first embodiment, and the description of the structure other than the support member 5 is omitted.

Third Embodiment

An open-type superconducting magnet device of the third embodiment will be described using FIG. 6.

Figure 6:
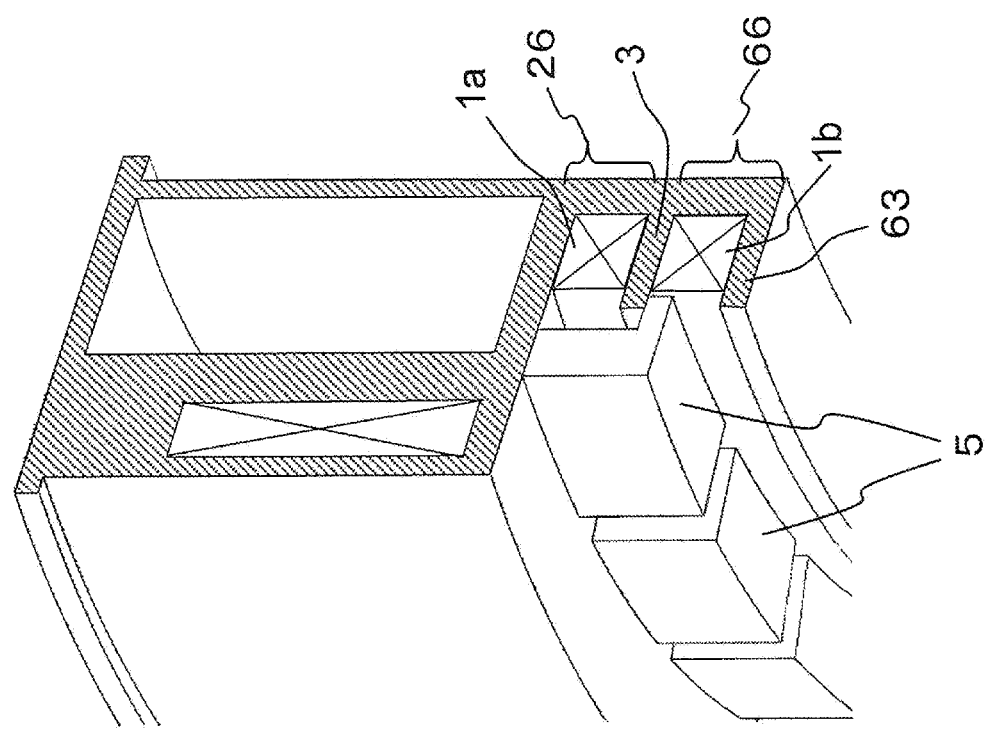
FIG. 6 is a cross-sectional perspective diagram of the coil bobbin 2 provided with the main coils 1a and 1b of the third embodiment in two stages.

The open-type superconducting magnet device of FIG. 6 is different from the first embodiment in the respect that the structure of the main coil bobbin 21 of the coil bobbin 2 has a two-stage structure.

That is, as shown in FIG. 6, the second cylindrical part 66 with the same structure as the cylindrical part 26 is connected to the end on the imaging space 40 side of the cylindrical part 26 of FIG. 2 across the end plate 3. The inner periphery part of the ring-shaped second end plate 63 is fixed to the end on the imaging space 40 side of the second cylindrical part 66. The second main coil 1b is wound around the second cylindrical part. The support member 5 supports the end plate 3 and does not support the second end plate 63.

Specifically, in the structure of FIG. 6, the second cylindrical part 66 and the second end plate 63 are disposed on the imaging space 40 side closer than the end plate 3 of the coil bobbin 21. The second cylindrical part 66 has the same structure as the cylindrical part 26 and is connected to the end on the imaging space 40 side of the cylindrical part 26. The inner periphery part of the second end plate 63 is fixed to the end on the imaging space 40 side of the cylindrical part 66 of the second cylindrical part 66, and the outer periphery part is opened. The second end plate 63 has a structure cantilever-supported by the second cylindrical part 66 similarly to the end plate 3.

Thus, the space inside the main coil bobbin 21 has a two-stage structure in the Z-axis direction (vertical direction). The upper main coil 1a and the lower main coil (the second main coil) 1b are wound on the upper space and lower space of the main coil 1 respectively.

In such a structure, a repulsive force to the shield coil 4 supported by the same coil bobbin 2 and an attractive force to the main coils 1 of the coil bobbins 2 disposed opposite to each other across an imaging space 40, as well as an electromagnetic force that the upper main coil 1a and the lower main coil 1b attract each other act on the upper main coil 1a and the lower main coil 1b similarly to the main coil 1 of the first embodiment. By adding up these forces, although a pulling force toward the equatorial plane (imaging space 40) side is applied to the upper main coil 1a, a pulling force toward the opposite side (the upper main coil 1a side) to the equatorial plane (imaging space 40) is applied to the lower main coil 1b.

Therefore, although a force to displace the second end plate 63 supporting the lower main coil 1b to the equatorial plane (imaging space) side is not generated in the structure of FIG. 6, the end plate 3 supporting the upper main coil 1a is pulled and displaced to the equatorial plane (imaging space 40) side. Therefore, in the structure of FIG. 6, the support member 5 is disposed so that it supports the end plate 3 in the Z direction, and the support member 5 is not disposed for the second end plate 63.

Thus, even in case of the structure where the main coils 1 are provided in two stages, the third embodiment can suppress deformation of the main coils 1 and prevent quench by preventing displacement of the end plate 3 using the support member 5.

Additionally, although the support member 5 has a shape divided in the peripheral direction similarly to the second embodiment in the structure of FIG. 6, the annular support member 5 can also be used as the first embodiment.

Because the other structures are similar to the first embodiment, the description is omitted.

Fourth Embodiment

Figure 7:
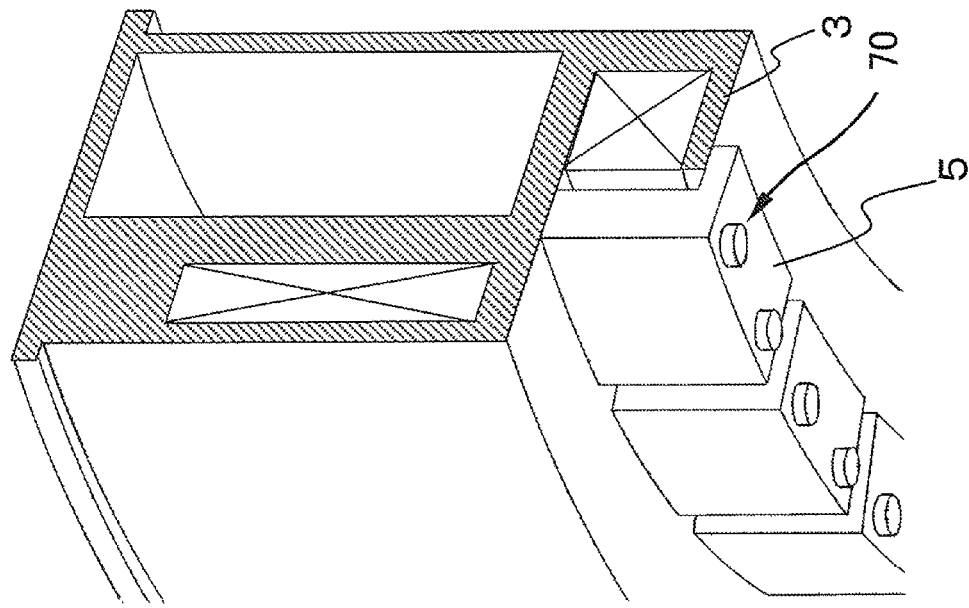
FIG. 7 is a cross-sectional perspective diagram of the coil bobbin 2 fixing a support member of the fourth embodiment with bolts.

As the fourth embodiment, the structure where the support member 5 is fixed to the coil bobbin 2 with the bolts 70 is shown in FIG. 7.

Through holes for the bolts 70 are provided on the support member 5, and threaded holes are provided on the opposite end plate 27 of the coil bobbin 2 or the end plate 31 of the shield coil bobbin 22. The bolts 70 are inserted in the through holes of the support member 5 and are screwed in the threaded holes provided on the opposite end plate 27 of the coil bobbin 2 or the end plate 31 of the shield coil bobbin 22. Hence, the support member 5 is fixed to the coil bobbin 2 firmly.

Although the support member 5 may be fixed to the coil bobbin 2 by welding as in the first embodiment, fixing with the bolts 70 can be performed easily compared to the case of fixing the support member 5 by welding as shown in FIG. 7. Also, by inserting a shim plate between the support member 5 and the coil bobbin 2, the height of the support member 5 can be adjusted easily. Additionally, the support member 5 can be comprised of not metal but FRP (Fiber Reinforced Plastics) by the structure of fixing the support member 5 with the bolts 70.

Also, a structure where through holes are provided on the opposite end plate 27 of the coil bobbin 2; threaded holes are provided on the upper surface of the support member 5; and the bolts 70 are inserted from the upper surface of the opposite end plate 27 (the opposite surface of the imaging space 40) to be screwed together with the support member 5 is also available.

A shape of the support member 5 is not limited to the divided shape as shown in FIG. 7, the ring-shaped support member 5 of FIG. 2 of the first embodiment and the support member 5 of the main coil bobbin 21 divided into the upper and lower two stages of the third embodiment can also be fixed with bolts as in the present embodiment naturally.

Fifth Embodiment

Figure 8:
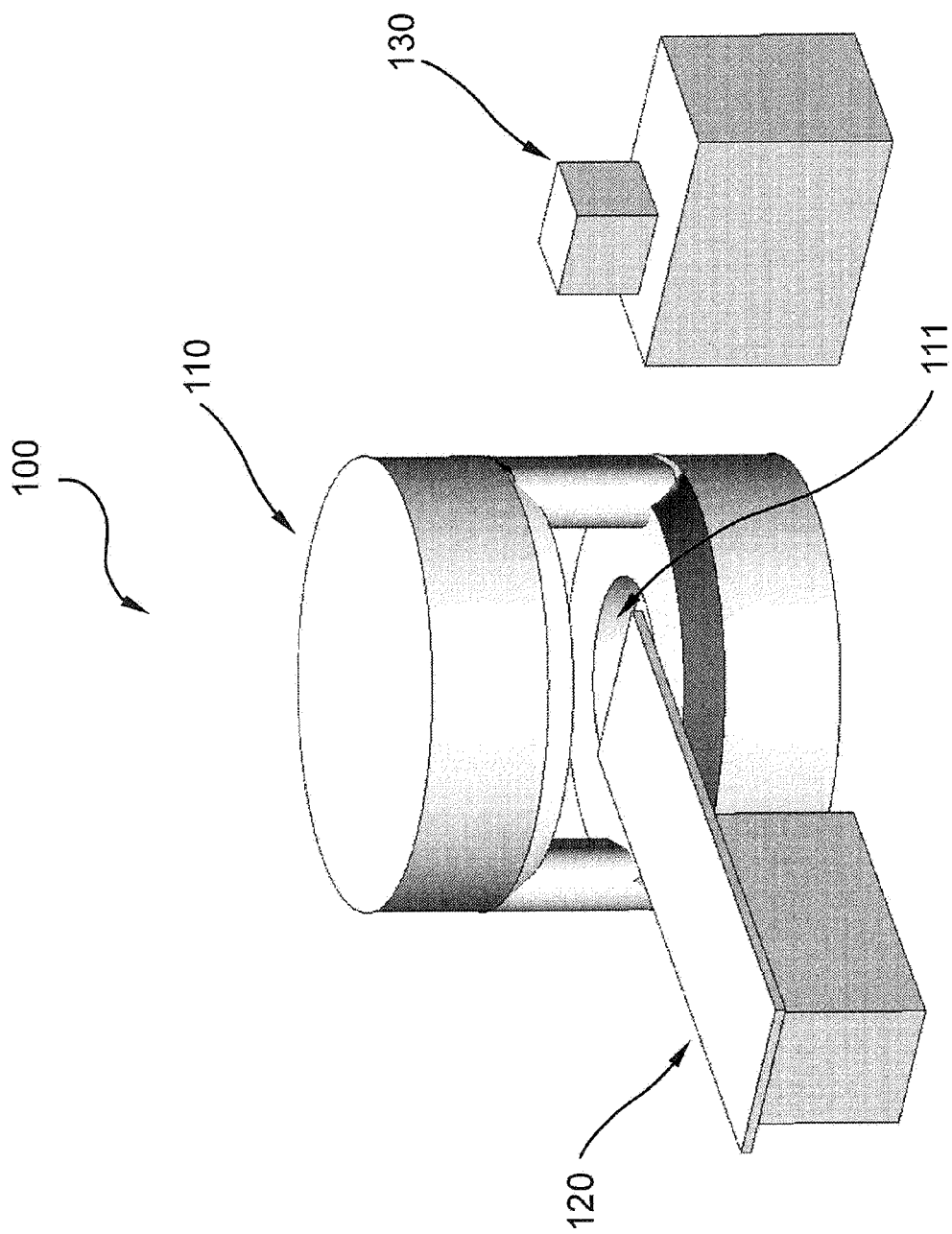
FIG. 8 is an explanatory diagram of an MRI device of the fifth embodiment.

As the fifth embodiment, an MRI device with the superconducting magnet device of the first to the fourth embodiments will be described using FIG. 8.

The MRI device 100 includes the superconducting magnet device 110, the bed 120 to insert an object in the static magnetic field space (imaging space) 40 created by the superconducting magnet device 110, a gradient magnetic field generating unit applying a gradient magnetic field to a static magnetic field space, a high-frequency magnetic field generating unit irradiating a high-frequency electromagnetic field to the static magnetic field space, a reception unit receiving a nuclear magnetic resonance signal generated by the object, and a signal processing unit reconstructing an object image from the nuclear magnetic resonance signal.

On the facing surface toward the imaging space 40 of the vacuum vessel 9 of the superconducting magnet device 110, the concave part 111 is formed, and a gradient magnetic field coil, a high-frequency irradiation coil, etc. are provided inside the concave part 111.

An object is placed on the bed 120, and it is inserted in the imaging space 40. A drive circuit outputting a drive current to a gradient magnetic field coil and a drive signal to a high-frequency irradiation coil, a detection circuit detecting an NMR signal received by a reception coil attached to the object, a signal processing unit reconstructing an image from a detected NMR signal, etc. are disposed in the control device 130. The control device 130 applies a gradient magnetic field to the object at a predetermined timing according to a pulse sequence directed by an operator and irradiates a high-frequency electromagnetic field. The signal processing unit receives an NMR signal generated from the object at the reception coil and reconstructs an image from the NMR signal to display on a display device.

An MRI device of the present embodiment is an open type that hardly gives a feeling of closeness to an object, and in addition to this, quench of a superconducting magnet hardly occurs, which can perform imaging for the object stably for a long period of time.

DESCRIPTION OF REFERENCE NUMERALS

1: main coil, 2: coil bobbin, 3: end plate, 4: shield coil, 5: support member, 6: connecting column, 7: liquid helium vessel, 8: shield plate, 9: vacuum vessel, 10: upper superconducting magnet, 20: lower superconducting magnet, 21: main coil bobbin, 22: shield coil bobbin, 23: housing part, 24: inner cylinder, 25: end plate, 26: cylindrical part, 26-1: inner periphery plate of the cylindrical part, 27: opposite end plate, 28: ring-shaped inner cylinder, 29: ring-shaped outer cylinder, 30: connecting part, 31: end plate, 32: opposite end plate, 40: imaging space, 63: center end plate, 70: bolt, 100: MRI device, 110: superconducting magnet device, 111: concave part, 120: bed, 130: control device

The invention claimed is:

1. A superconducting magnet device including:
a pair of superconducting magnets disposed opposite to each other across a space to create a static magnetic field and a connecting part connecting a pair of the superconducting magnets,
wherein each of the superconducting magnets is comprised of a main coil, a shield coil to suppress a leakage magnetic field of the main coil, and a coil bobbin, and
the coil bobbin has a first cylindrical part on which the main coil is wound, a ring-shaped end plate whose inner periphery part is fixed to an end on the space side of the first cylindrical part, and a support member preventing the outer periphery part of the ring-shaped end plate from being displaced on the space side, and wherein
a second cylindrical part with the same shape as the first cylindrical part of the coil bobbin is connected to the end on the space side of the first cylindrical part across the ring-shaped end plate, and the inner periphery part of a ring-shaped second end plate is fixed to the end on the space side of the second cylindrical part, and
a second main coil is wound around the second cylindrical part; and
the support member supports the ring-shaped end plate and does not support the second ring-shaped end plate.

2. The superconducting magnet device according to claim 1,
wherein the coil bobbin further includes a ring-shaped opposite end plate disposed on the opposite side to a space of the first cylindrical part, and
the support member is a member with an L-shaped cross-section of which an end is fixed to the opposite end plate; and the other end supports the outer periphery part of the ring-shaped end plate.

3. The superconducting magnet device according to claim 2,
wherein the support member is a ring-shaped member along the ring-shaped end plate.

4. The superconducting magnet device according to claim 2,
wherein the support member is a plurality of members disposed along the peripheral direction of the ring-shaped end plate.

5. The superconducting magnet device according to claim 4,
wherein a plurality of the members of the support member are disposed at intervals mutually.

6. The superconducting magnet device according to claim 2,
wherein the support member is fixed to the opposite end plate with bolts.

7. A magnetic resonance imaging device including:
a superconducting magnet device;
a bed inserting an object in a static magnetic field space created by the superconducting magnet device;
a gradient magnetic field generating unit applying a gradient magnetic field to the static magnetic field space;
a high-frequency magnetic field generating unit irradiating a high-frequency magnetic field to the static magnetic field space;
a reception unit receiving a nuclear magnetic resonance signal generated by the object; and
a signal processing unit reconstructing an image of the object from the nuclear magnetic resonance signal,
wherein the superconducting magnet device is a superconducting magnet device according to claim 1.

* * * * *